(12) United States Patent
Williams et al.

(10) Patent No.: US 7,069,797 B2
(45) Date of Patent: Jul. 4, 2006

(54) SIMPLIFIED BIOFIDELIC LOWER LEG SURROGATE

(75) Inventors: Kevin Williams, Quebec (CA); Daniel Bourget, Stoneham (CA); Duane Cronin, Waterloo (CA); Denis Bergeron, Adelaide (AU); Christopher Salisbury, Waterloo (CA)

(73) Assignee: Her Majesty the Queen as represented by the Minister of National Defence of Her Majesty's Canadian Government, Ottawa (CA)

( * ) Notice: Subject to any disclaimer, the term of this patent is extended or adjusted under 35 U.S.C. 154(b) by 471 days.

(21) Appl. No.: 10/648,793

(22) Filed: Aug. 27, 2003

(65) Prior Publication Data

US 2004/0117035 A1   Jun. 17, 2004

Related U.S. Application Data

(60) Provisional application No. 60/406,949, filed on Aug. 30, 2002.

(51) Int. Cl.
*G01M 19/00*  (2006.01)
(52) U.S. Cl. .................................... 73/866.4
(58) Field of Classification Search ............... 73/866.4, 73/865.1, 865.4, 865.6; 434/262, 267, 270, 434/274
See application file for complete search history.

(56) References Cited

U.S. PATENT DOCUMENTS

| 4,701,132 A |   | 10/1987 | Groesch et al. ............. 434/274 |
| 5,018,977 A |   | 5/1991 | Wiley et al. ................ 434/274 |
| 5,589,651 A | * | 12/1996 | Viano et al. ............... 73/866.4 |
| 5,648,915 A |   | 7/1997 | McKinney et al. ......... 382/141 |
| 6,923,081 B1 | * | 8/2005 | Krstic ....................... 73/866.4 |
| 2003/0183025 A1 |   | 10/2003 | Krstic ...................... 73/866 A |

* cited by examiner

*Primary Examiner*—Hezron Williams
*Assistant Examiner*—Tamiko Bellamy
(74) *Attorney, Agent, or Firm*—Stites & Harbison PLLC; Ross F. Hunt, Jr.

(57) ABSTRACT

A biofidelic lower leg surrogate includes a latex skin containing tissue simulating gelatin and a simulative bone assembly. The bone assembly is defined by a hollow, cylindrical, polymeric tibia body connected to an ankle piece in the shape of a section of a solid cylinder; a pair of heel blocks bonded to each other and to the ankle piece with a triangular bottom opening therebetween defining an arch; a nylon tendon strip mounted in grooves in the bottom of the heel blocks; and a heel pad extending across the bottom of the blocks.

13 Claims, 2 Drawing Sheets

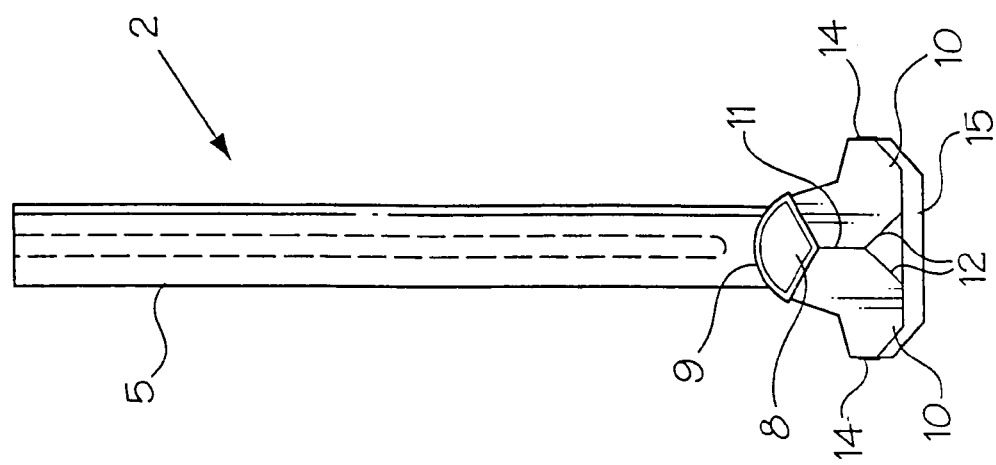
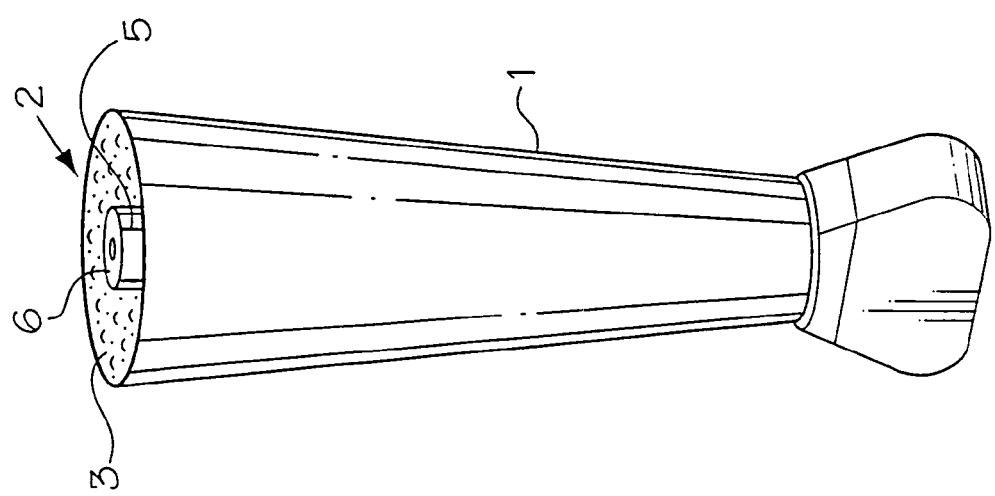

SIMPLIFIED BIOFIDELIC LOWER LEG SURROGATE

This application claims benefit of U.S. Provisional Application No. 60/406,949, filed Aug. 30, 2002.

FIELD OF THE INVENTION

The present invention relates to a lower leg surrogate and, in particular to a simplified, biofidelic lower leg surrogate designed to test protective footwear for personnel involved in military operations where land mines may exist.

BACKGROUND OF THE INVENTION

With the large number of mines laid around the world, the protection of personnel involved in military operations, military demining and humanitarian demining against antipersonnel (AP) mines is exceedingly important. The design of protective footwear is particularly challenging. Test procedures for protective footwear are not well established and many of the current evaluation tools for protective footwear are complex, expensive to manufacture, show poor repeatability, give poor prediction of injury outcome or have strong ethical considerations.

There are a number of test methods that have been or are currently used around the world to evaluate protective boots for personnel involved in operations where mines may be located. These are listed below along with problems and/or limitations associated with each method.

1. Non-frangible leg. A non-frangible surrogate provides only indirect prediction of injury. The fracturing of a leg and the disruption of tissue influence performance of a protection system, and such events will not be captured by a non-frangible system.

2. Biological surrogates. These surrogates create a biohazard, do not provide an accurate representation of human bone and there is a variability of geometrical and mechanical properties.

3. Cadaver testing. This type of testing creates a biohazard and there is a variability of geometrical and mechanical properties. Moreover, ethical issues exist for this type of testing, and the expense and availability limit such testing.

4. Complex, biofidelic, frangible surrogate legs, i.e. the existing frangible synthetic legs. Such legs are expensive and complex.

SUMMARY OF THE INVENTION

The object of the present invention is to provide a simple biofidelic lower leg surrogate, which is relatively easy and inexpensive to manufacture.

Accordingly, the invention relates to a lower leg surrogate comprising:
(a) an outer skin formed of a flexible, resilient material;
(b) a tissue resembling gel encased in said skin;
(c) a simulative bone assembly in said gel, said bone assembly including:
  (i) an elongated cylindrical tibia body;
  (ii) an ankle piece bonded to a bottom end of said tibia body;
  (iii) at least one heel block bonded to said ankle piece, said heel block having an arch at the bottom thereof; and
  (iv) a heel pad extending across the bottom of the heel block and the arch.

BRIEF DESCRIPTION OF THE DRAWINGS

The invention is described below in greater detail with reference to the accompanying drawings, in which:

FIG. 1 is an isometric view of a biofidelic lower leg surrogate in accordance with the present invention;

FIG. 2 is a front view of an interior bone assembly used in the lower leg surrogate of FIG. 1;

Figure 4:
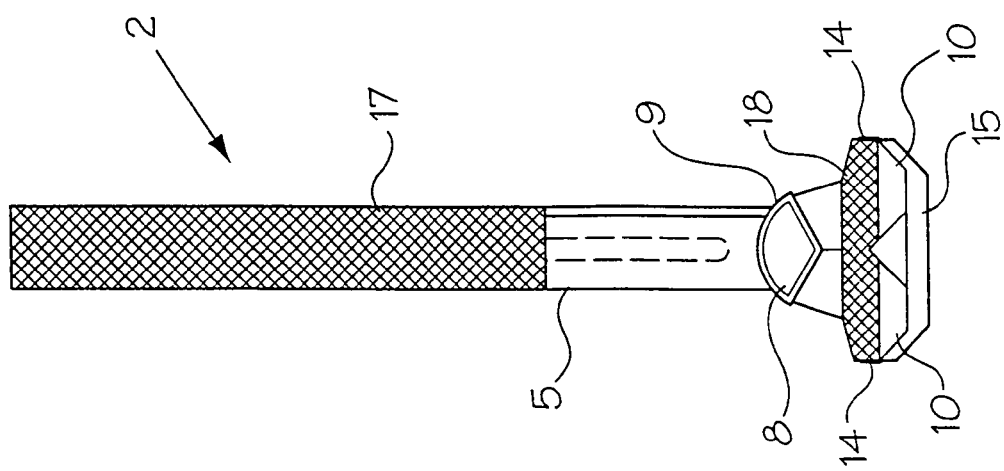
FIG. 4 is a front view of the bone assembly with gauze attached thereto.

Referring to the drawings, the basic elements of the lower leg surrogate include an external latex skin 1 covering all but the upper end of an interior simulative bone assembly indicated generally at 2, and a ballistic gelatin filler 3 between the skin 1 and the bone assembly 2.

Figure 3:
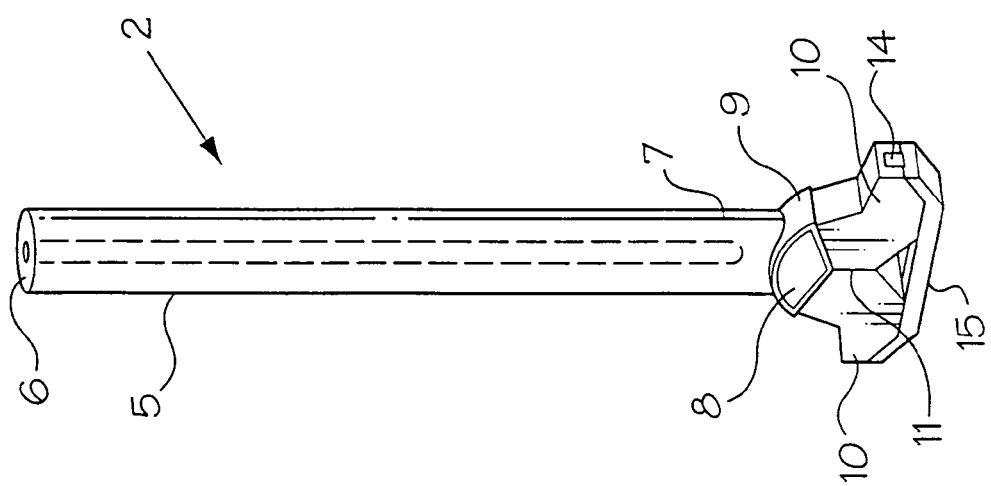
FIG. 3 is an isometric view of the assembly of FIG. 2.

As best shown in FIGS. 2 to 4, the interior bone assembly includes a hollow, fiber reinforced, polymeric, cylindrical body 5 simulating the tibia of a leg. A suitable fiber reinforced polymer for use in the tibia body 5 is available from Pacific Research Laboratories. The body 5 is formed by injection molding a cylinder with a hollow center defined by a passage extending from the upper end 6 to a location proximate the lower end 7 thereof. The tibia body 5 is mounted on a simulative talus (ankle) piece 8, which has the shape of a section of a solid cylinder with a convex top surface and inclined straight bottom surfaces (not shown) extending to a location beneath the longitudinal axis of the cylindrical body 5. An RTV (room temperature vulcanizing) silicone, cartilage simulative diaphragm 9 covers the convex top surface and the inclined bottom surfaces of the talus piece 8. A preferred RTV silicone is RTV664.

The talus piece 8 is bonded to the body 5 and to two simulative calcaneus (heel) blocks 10 using silicone adhesive. Like the talus piece 8, the blocks 10 are formed of a rigid, cellular polyurethane foam coated with fiber reinforced epoxy resin. A suitable fiber reinforced polymer and a cellular polyurethane foam for use in the talus piece 5 and in the calcaneus blocks 10 are available from Pacific Research Laboratories. The blocks 10 are generally C-shaped with abutting inner sides 11, and inclined top surfaces for receiving the bottom surfaces of the talus piece 8. The lower ends 12 (FIG. 1) of the inner sides of the blocks 10 are inclined, whereby an inverted V-shaped notch is formed when the blocks abut in a back-to-back relationship. The front portion of the foot is not simulated explicitly, because the most serious injuries as a result of an explosion are those that occur in the calcaneus (heel) bone and the major damage in the tibia is caused by force transmitted through the heel. Accordingly, two heel blocks 10 are used, extending downwardly in opposite directions from the tibia body 5 and the talus piece 8.

A thin, tendon-defining nylon strip 14 (FIG. 3) extends from the vertical outer side of one block 10, along the bottom of such one block, across the bottom of the triangular notch between the blocks, along the bottom of the other block and up the vertical outer side of such other block 10. The strip 14 is located in a rectangular groove located in the top surface of an RTV silicone heel pad 15, which is coextensive with the tendon strip 14. The strip 14 is bonded to each block 10 along the entire contact surfaces therebetween using an epoxy adhesive. A suitable RTV silicone for the heel pad 15 is RTV-7888-10, which is a less stiff silicone rubber than RTV664 preferably used in the cartilage diaphragm 9.

The surrogate lower leg is completed by bonding gauze covers 17 and 18 to the tibia body 5 and to the calcaneus blocks 10, and covering the simulative bone assembly with the gelatinous simulative soft tissue 3 and the skin 1.

In producing the lower leg surrogate, tibia body 5 and the rigid, cellular polyurethane components defining the talus and calcaneus bones are molded separately. In the case of the talus and calcaneus bones, a fiber reinforced epoxy resin cover is injection molded around polyurethane cores of the components. The simulative bones are bonded together using silicone adhesive, except for the tendon strip 14, which is bonded to the calcaneus blocks 10 with epoxy. The gauze covers 17 and 18 are bonded to the tibia body 5 and the calcaneus blocks 10 using epoxy.

A two-piece fiberglass mold (not shown) is used to mold the finished leg. A latex preform skin 1 fabricated using a positive mold of the leg is used to line the mold. The bone assembly 2 is carefully inserted into the latex skin 1, which is then placed in the mold. Small knobs (not shown) in the lower part of the mold mate with indentations in the silicone heel pad 15 to align the foot and to ensure that the bone assembly is centered in the mold. The top of the tibia body 5 is clamped with an external fixture to the fiberglass mold, again to ensure correct alignment of the bone assembly 2 in the finished leg. The ballistic gelatin is prepared in accordance with established procedures and poured into the latex skin in the mold. The gauze strips 17 and 18 provide a bond between the bone assembly 2 and the gelatinous filler 3. The surrogate leg is left to cool in a refrigerator until it reaches 4° C. Once the gelatin has solidified, the mold is removed for reuse.

We claim:

1. A lower leg surrogate comprising:
    (a) an outer skin formed of a flexible, resilient material;
    (b) a tissue resembling gel encased in said skin;
    (c) a simulative bone assembly in said gel, said bone assembly including:
        (i) an elongated cylindrical tibia body;
        (ii) an ankle piece bonded to a bottom end of said tibia body;
        (iii) at least one heel block bonded to said ankle piece, said heel block having an arch at the bottom thereof; and
        (iv) a heel pad extending across the bottom of the heel block and the arch.

2. The lower leg surrogate of claim 1, including a pair of heel blocks bonded to each other and to said ankle piece, said heel blocks being shaped to define said arch at the bottom center of the assembly.

3. The lower leg surrogate of claim 2, including a tendon strip in a bottom surface of each said heel block.

4. The lower leg surrogate of claim 1, wherein said outer skin is formed of latex.

5. The lower leg surrogate of claim 1, wherein said gel is gelatin.

6. The lower leg surrogate of claim 1, wherein said tibia body is formed of a fiber reinforced polymer.

7. The lower leg surrogate of claim 6, wherein said ankle piece and said heel blocks are formed of rigid, cellular polyurethane.

8. The lower leg surrogate of claim 7, wherein said ankle piece and said heel blocks are coated with a fiber reinforced epoxy resin.

9. The lower leg surrogate of claim 8, wherein said heel pad is formed of a room temperature vulcanizing silicone.

10. The lower leg surrogate of claim 3, including a cartilage simulative diaphragm on surfaces of said ankle piece abutting said tibia body and said heel blocks.

11. The lower leg surrogate of claim 10, wherein said ankle piece has the shape of a section of a cylinder with a convex top surface connected to a bottom end of said tibia body and inclined bottom surfaces bonded to top ends of said heel blocks.

12. The lower leg surrogate of claim 11, wherein said diaphragm is formed of room temperature vulcanizing silicone.

13. The lower leg surrogate of claim 10, including a gauze cover on at least a portion of each of said tibia body and said heel blocks for providing a mechanical link between the bone assembly and the gel.

* * * * *